United States Patent
Lautamo

(10) Patent No.: US 10,143,958 B2
(45) Date of Patent: Dec. 4, 2018

(54) RETICULATED ANNULAR CAPILLARY GAS CHROMATOGRAPHY COLUMN AND METHOD FOR FORMING RETICULATED ANNULAR CAPILLARY GAS CHROMATOGRAPHY COLUMN

(71) Applicant: RESTEK CORPORATION, Bellefonte, PA (US)

(72) Inventor: Roy M. A. Lautamo, Placerville, CA (US)

(73) Assignee: RESTEK CORPORATION, Bellefonte, PA (US)

( * ) Notice: Subject to any disclaimer, the term of this patent is extended or adjusted under 35 U.S.C. 154(b) by 206 days.

(21) Appl. No.: 15/381,328

(22) Filed: Dec. 16, 2016

(65) Prior Publication Data

US 2017/0173513 A1 Jun. 22, 2017

Related U.S. Application Data

(60) Provisional application No. 62/268,591, filed on Dec. 17, 2015.

(51) Int. Cl.
*B01D 53/02* (2006.01)
*G01N 30/60* (2006.01)
(Continued)

(52) U.S. Cl.
CPC ............ *B01D 53/025* (2013.01); *B33Y 10/00* (2014.12); *B33Y 80/00* (2014.12);
(Continued)

(58) Field of Classification Search
CPC ........... G01N 30/6069; G01N 30/6078; G01N 30/6043; G01N 30/6017; B01D 53/025; B33Y 10/00; B33Y 80/00
See application file for complete search history.

(56) References Cited

U.S. PATENT DOCUMENTS

| | | |
|---|---|---|
| 4,995,163 A | 2/1991 | Golay |
| 7,273,517 B1 | 9/2007 | Lewis et al. |
| 2006/0000238 A1 | 1/2006 | Griffin et al. |

FOREIGN PATENT DOCUMENTS

| | | |
|---|---|---|
| CN | 105092746 | 11/2015 |
| FR | 2409786 A1 | 6/1979 |

OTHER PUBLICATIONS

M. Golay, "Preparative Capillary Chromatography-A Proposal," Journal of High Resolution Chromatography & Chromatography Communications, vol. 11, Jan. 1998, pp. 6-8.
(Continued)

*Primary Examiner* — Robert Clemente
(74) *Attorney, Agent, or Firm* — McNees Wallace & Nurick LLC

(57) ABSTRACT

A reticulated annular capillary GC column is disclosed including a capillary wall, a core disposed within the capillary wall, an annulus disposed between the capillary wall and the core, and vanes disposed in the annulus. The vanes extend along the length of the capillary wall for less than the length of the capillary wall. The vanes define a reticulated flow path through the annulus. The vanes structurally support the core within the capillary wall. A method for forming the reticulated annular capillary GC column is disclosed including forming a preform master pattern by an additive manufacturing technique, the preform master pattern including a preform wall, a preform core, a preform annulus disposed between the preform wall and the preform core, and struts disposed in the preform annulus. A preform is cast from the preform master pattern, and the preform is drawn down, forming the reticulated annular capillary GC column.

20 Claims, 5 Drawing Sheets

(51) Int. Cl.
*B33Y 10/00* (2015.01)
*B33Y 80/00* (2015.01)

(52) U.S. Cl.
CPC ..... *G01N 30/6069* (2013.01); *G01N 30/6078* (2013.01); *G01N 30/6043* (2013.01)

(56) References Cited

OTHER PUBLICATIONS

C. Fee, et al., "3D Printed Porous Media Columns With Fine Control of Colummn Packing Morphology," Journal of Chromatography A, 2014, pp. 18-24.
LC GC, "3D Printing—A Coming Revolution?", The Column, vol. 10, Issue 9, May 22, 2014, 2 pgs, http://www.chromatographyonline.com/3d-printing-coming-revolution.
F. Lucklum, et al., Miniature 3D gas chromatography columns with integrated fluidic connectors using high-resolution stereolithography fabrication, ScienceDirect, Procedia Engineering 120 (2015) 703-706.
Conan Fee, et al., 3D printed porous media columns with fine control of column packing morphology, Journal of Chromatography A, 1333 (2014) 18-24.

RETICULATED ANNULAR CAPILLARY GAS CHROMATOGRAPHY COLUMN AND METHOD FOR FORMING RETICULATED ANNULAR CAPILLARY GAS CHROMATOGRAPHY COLUMN

CROSS-REFERENCE TO RELATED APPLICATIONS

This application claims the benefit of U.S. Provisional Patent Application No. 62/268,591, filed Dec. 17, 2015, entitled "Reticulated Annular Capillary Gas Chromatography Column and Method for Forming Reticulated Annular Capillary Gas Chromatography Column," the disclosures of which are incorporated by reference in its entirety and made part of the present U.S. utility patent application for all purposes.

FIELD OF THE INVENTION

This application is directed to capillary gas chromatography ("GC") columns and methods for forming capillary GC columns. More specifically, this application is directed to reticulated annular capillary GC columns and methods for forming reticulated annular capillary GC columns.

BACKGROUND OF THE INVENTION

The usage of capillary columns for GC first began in the late 1950s. Although there have been significant iterative advancements in the six decades since, the fundamental capillary format has remained essentially the same. Column capacity remains limited by the small diameter within the capillary, and the inverse relationship between column efficiency and column diameter. Although column efficiency increases as the column diameter decreases, column capacity decreases exponentially with decreasing diameter, and back pressure increases exponentially with decreasing diameter. For example, decreasing the inner diameter of a capillary column from 0.32 mm to 0.25 mm results in a reduction in column capacity of about 40%. Thus, the column efficiency is effectively limited by countervailing process constraints.

Multibore capillary columns have been proposed many times in the six decades since the introduction of the capillary column for GC, however these multibore capillary columns have never been successfully commercialized due to significant drawbacks in their implementation. One disadvantage of multibore capillary columns is that each bore must have the same passage rate (dead time), and the acceptable variance cannot exceed 0.1%, which is difficult to achieve. Further, back-pressure still increases exponentially with reduction of diameter, and so each bore gives rise to significant back pressure. The necessary compromises inherent in multibore capillary columns have proven to be untenable.

Another proposal for improving column capacity while maintaining column efficiency, based on theoretical calculations, has been a capillary with a rectangular cross-section. In order to overcome differential drag at the ends of the rectangular cross-section, it has been proposed to bend the ends of the rectangular channel around to meet one another, forming an annulus, but an arrangement to support the center core of the annulus running throughout the capillary has proved elusive. Both fiber-in-capillary and helical fiber supports (see U.S. Pat. No. 4,665,163) have failed to provide useful and effective structures.

Accordingly, it would be desirable to provide capillary columns and methods for forming capillary columns not suffering from the above-described drawbacks.

BRIEF DESCRIPTION OF THE INVENTION

In one exemplary embodiment, a reticulated annular capillary GC column comprises at least one capillary wall, a core disposed within the capillary wall, at least one annulus disposed between the at least one capillary wall and the core, and a plurality of vanes disposed in the at least one annulus. The at least one capillary wall includes a wall length, a wall inner diameter, and a wall outer diameter. The core includes a core outer diameter. Each of the plurality of vanes extends along the wall length and for less than the wall length. The plurality of vanes defines a reticulated flow path through the at least one annulus. The plurality of vanes structurally support the core within the at least one capillary wall.

In another exemplary embodiment, a method for forming a reticulated annular capillary GC column comprises forming a preform master pattern by an additive manufacturing technique. The preform master pattern includes an antecedent conformation, wherein the antecedent conformation includes at least one preform wall, a preform core having a preform core diameter disposed within the at least one preform wall, at least one preform annulus disposed between the at least one preform wall and the preform core, and a plurality of struts disposed in the at least one preform annulus. The plurality of struts structurally support the preform core within the at least one preform wall. The method further comprises casting a preform from the preform master pattern, wherein the preform includes the antecedent conformation. The preform is drawn down, forming the reticulated annular capillary GC column. Drawing down the preform includes lengthening and narrowing the at least one preform wall, forming at least one capillary wall, wherein the at least one capillary wall includes a wall length, a wall inner diameter, and a wall outer diameter. Drawing down the preform also includes lengthening and narrowing the preform core to form a core, narrowing the preform core diameter to a core outer diameter. Drawing down the preform further includes lengthening and narrowing the plurality of struts, forming a plurality of vanes. Each of the plurality of vanes extends along the wall length and for less than the wall length. The plurality of vanes defines a reticulated flow path through the at least one annulus, and the plurality of vanes structurally support the core within the at least one capillary wall.

BRIEF DESCRIPTION OF THE DRAWINGS

Wherever possible, the same reference numbers will be used throughout the drawings to represent the same parts.

DETAILED DESCRIPTION OF THE INVENTION

Figure 1:
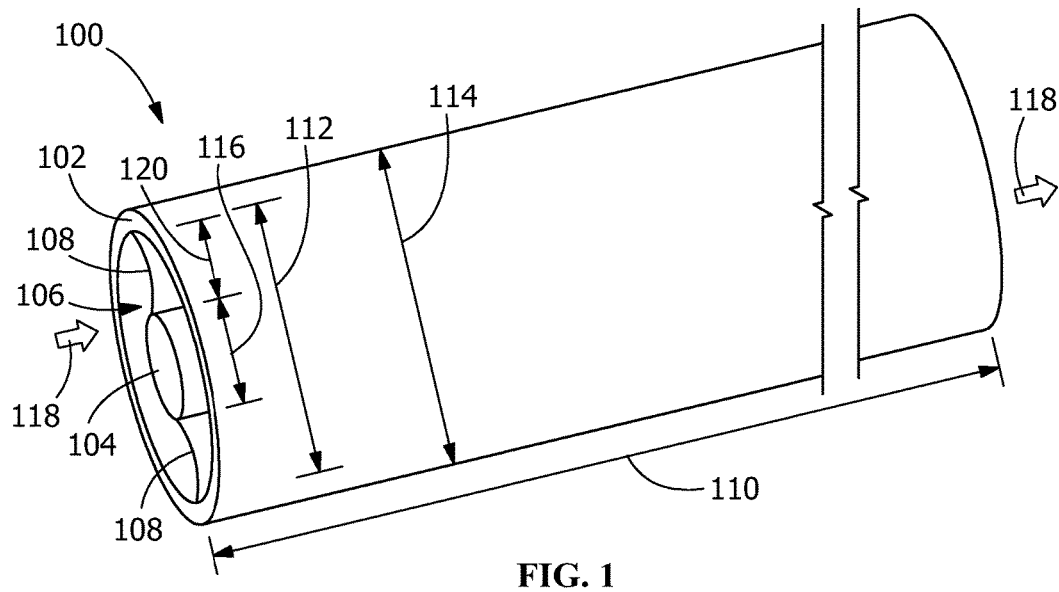
FIG. 1 is a perspective view of a reticulated annular capillary GC column, according to an embodiment of the present disclosure.

Referring to FIG. 1, in one embodiment, a reticulated annular capillary GC column 100 comprises at least one capillary wall 102, a core 104 disposed within the capillary wall 102, at least one annulus 106 disposed between the at least one capillary wall 102 and the core 104, and a plurality of vanes 108 disposed in the at least one annulus 106. The at least one capillary wall 102 includes a wall length 110, a wall inner diameter 112, and a wall outer diameter 114. The core 104 includes a core outer diameter 116. Each of the plurality of vanes 108 extends along the wall length 110 and for less than the wall length 110. The plurality of vanes 108 defines a reticulated flow path 118 through the at least one annulus 106, and the annulus defines an annular gap 120 between the at least one capillary wall 102 and the core 104. The plurality of vanes 108 structurally support the core 104 within the at least one capillary wall 102.

Figure 2:
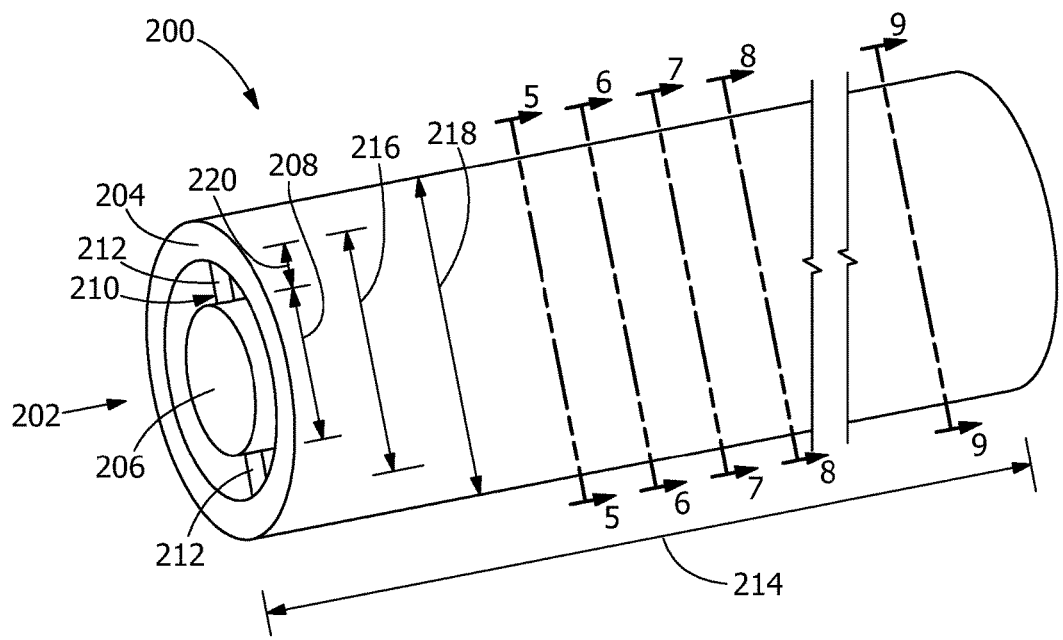
FIG. 2 is a perspective view of a preform master pattern, according to an embodiment of the present disclosure.
Figure 3:
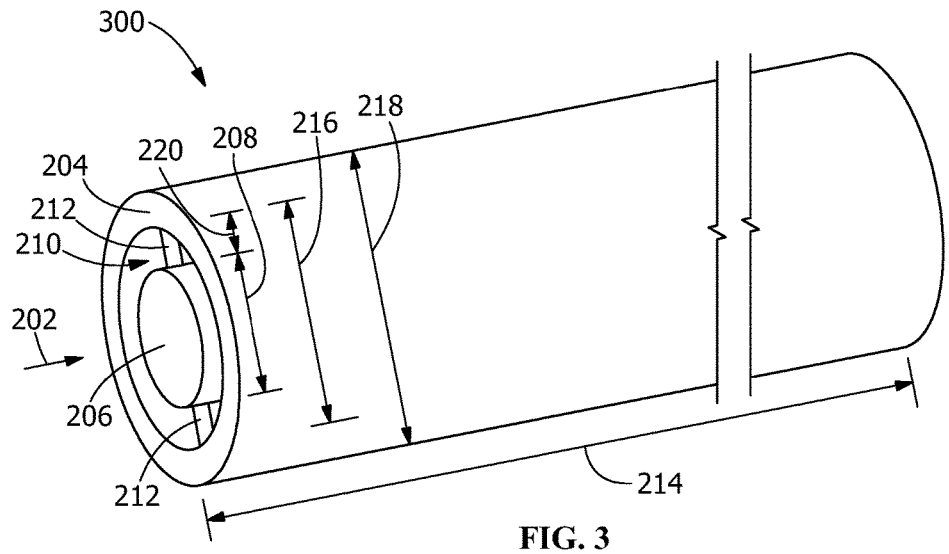
FIG. 3 is a perspective view of a preform, according to an embodiment of the present disclosure.

Referring to FIGS. 2 and 3, in one embodiment, a method for forming the reticulated annular capillary GC column 100 (see FIG. 1) includes forming a preform master pattern 200 by an additive manufacturing technique. The preform master pattern 200 includes an antecedent conformation 202, wherein the antecedent conformation 202 includes at least one preform wall 204 having a preform wall inner diameter 216, a preform wall outer diameter 218, and a preform wall length 214, a preform core 206 having a preform core diameter 208 disposed within the at least one preform wall 204, at least one preform annulus 210 disposed between the at least one preform wall 204 and the preform core 206, and a plurality of struts 212 disposed in the at least one preform annulus 210. The plurality of struts 212 structurally support the preform core 206 within the at least one preform wall 204. The method further comprises casting a preform 300 from the preform master pattern 200, wherein the preform 300 includes the antecedent conformation 202.

Referring to FIGS. 1 and 3, the preform 300 is drawn down, forming the reticulated annular capillary GC column 100. Drawing down the preform 300 includes lengthening and narrowing the at least one preform wall 204, forming the at least one capillary wall 102, wherein the at least one capillary wall 102 includes the wall length 110, the wall inner diameter 112, and the wall outer diameter 114. Drawing down the preform 300 also includes lengthening and narrowing the preform core 206 to form the core 104, narrowing the preform core diameter 208 to the core outer diameter 116. Drawing down the preform 300 further includes lengthening and narrowing the plurality of struts 212, forming the plurality of vanes 108. Each of the plurality of vanes 108 extends along the wall length 110 and for less than the wall length 110. The plurality of vanes 108 defines the reticulated flow path 118 through the at least one annulus 106, and the plurality of vanes 108 structurally support the core 104 within the at least one capillary wall 102.

Figure 4:
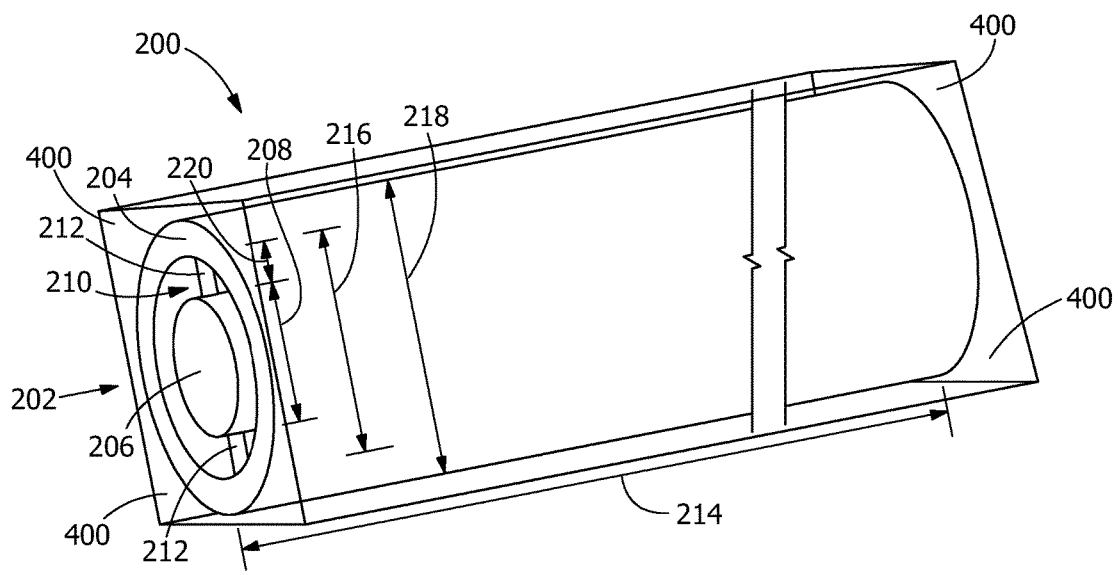
FIG. 4 is a perspective view of a preform master pattern interpolated with support material, according to an embodiment of the present disclosure.

Referring to FIGS. 2 and 4, the additive manufacturing technique used to form the preform master pattern 200 may be any suitable additive manufacturing technique, including, but not limited to, three-dimensional printing (such as, by way of example, with a SOLIDSCAPE 3Z Pro 3D three-dimensional printer), although three-dimensional printing is a rapidly evolving technical endeavor, and there are constant advancements in achievable resolution and material options, as well as new machines incorporating these advancements. In one embodiment, the additive manufacturing technique may form the preform master pattern 200 interpolated with a support material 400. One or both of the preform master pattern 200 and the support material 400 may be formed from a wax material. Inclusion of the support material 400, which is optional, may be useful for forming certain features which would otherwise be unsupported during the production process, and would therefore be difficult or impossible to form reproducibly and accurately.

In an embodiment incorporating the support material 400, the support material 400 may be removed by any suitable technique which removes the support material 400 while leaving the preform master pattern 200 essentially undisturbed. In one embodiment, wherein the support material 400 is a wax, the preform master pattern 200 interpolated with the support material 400 is submerged in a solvent bath to dissolve the support material 400. The solvent bath may be heated. Following solvent bath treatment, the preform master pattern 200 is isolated.

In another embodiment, other additive manufacturing techniques which may be adapted to form the preform master pattern 200 include, but are not limited to, fused deposition modeling, fused filament fabrication, stereolithography, continuous liquid interface production, or combinations thereof. These other additive manufacturing techniques may be used in conjunction with three-dimensional printing, with or without an interpolated support material 400.

Figure 5:
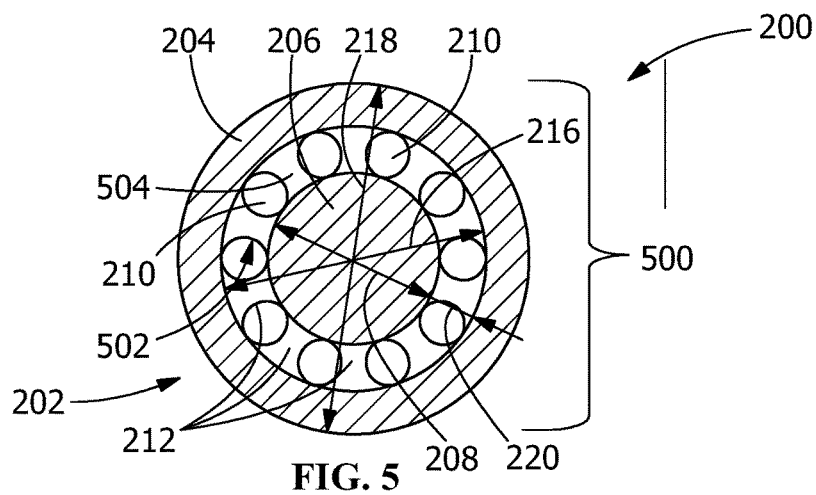
FIG. 5 is a sectional view along lines 5-5 of the preform master pattern of FIG. 2, according to an embodiment of the present disclosure.
Figure 6:
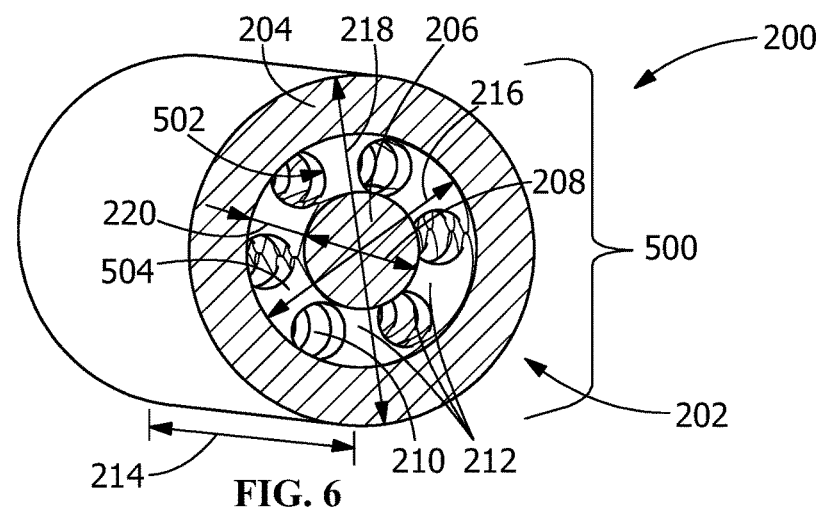
FIG. 6 is a sectional view along lines 6-6 of the preform master pattern of FIG. 2, according to an embodiment of the present disclosure.
Figure 7:
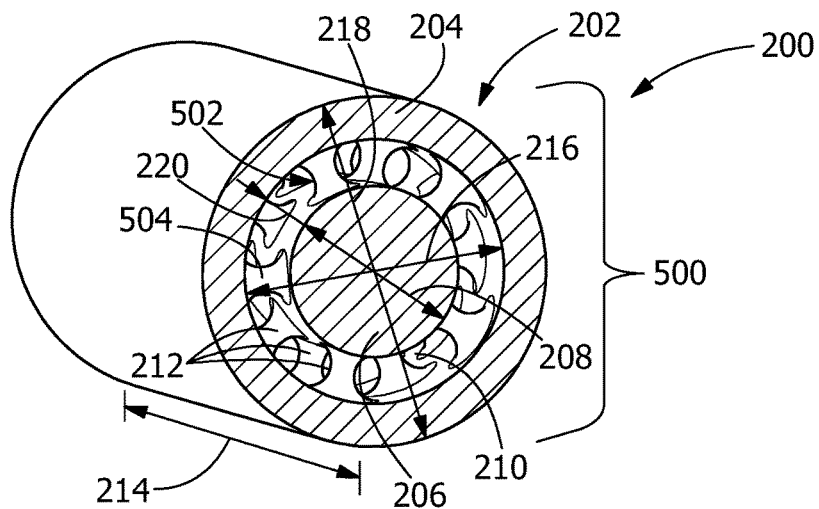
FIG. 7 is a sectional view along lines 7-7 of the preform master pattern of FIG. 2, according to an embodiment of the present disclosure.

Referring to FIGS. 5-7, the plurality of struts 212 of the preform master pattern 200 may be arranged in any suitable pattern (replicated in the preform 300 formed from the preform master pattern 200). In one embodiment, the plurality of struts 212 are organized into radial clusters 500 along the preform wall length 214, in which each radial cluster 500 is distributed about the preform core 206. The distribution of the plurality of struts 212 around the preform core 206 may be symmetric (shown) or asymmetric (not shown). Each radial cluster 500 may include the same number within the plurality of struts 212 (shown) or the number within the plurality of struts 212 at each radial cluster 500 may differ independently (not shown). Subsequent radial clusters 500 may be aligned with one another (FIG. 6) or may be offset (FIG. 7). Where the subsequent radial clusters 500 are offset, the offset between each subsequent radial cluster 500 may be constant (FIG. 7) or may vary independently (not shown). The shape of each of the plurality of struts 212 in a radial cluster 500 may be the same (shown) or different (not shown), and the shape of each of the plurality of struts 212 between subsequent radial clusters 500 may be the same (shown) or different (shown). Each radial cluster 500 may include one or more of the plurality of struts 212.

Figure 8:
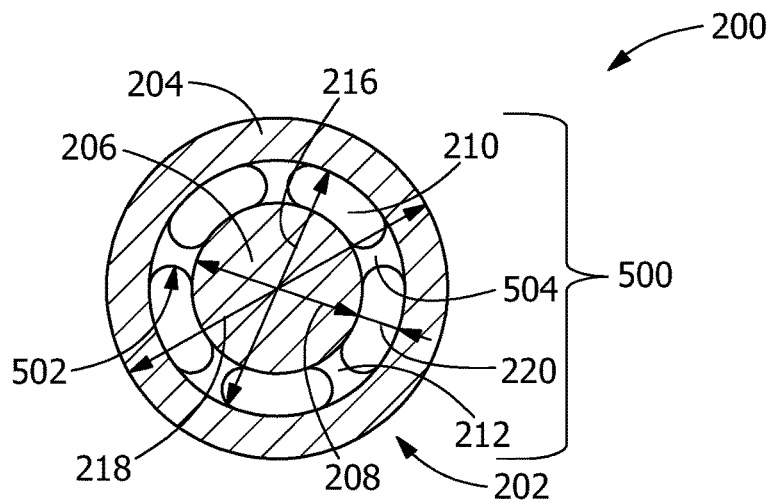
FIG. 8 is a sectional view along lines 8-8 of the preform master pattern of FIG. 2, according to an embodiment of the present disclosure.

Referring to FIG. 8, in one embodiment, a radial cluster 500 of a plurality of struts 212 in a preform master pattern 200 includes a preform wall outer diameter 218 of about 8 mm and the preform core 206 includes a preform core diameter 208 of about 4 mm. The radial cluster 500 of the plurality of struts 212 includes five struts 212 distributed symmetrically about the preform core 206 at 72° intervals.

Figure 9:
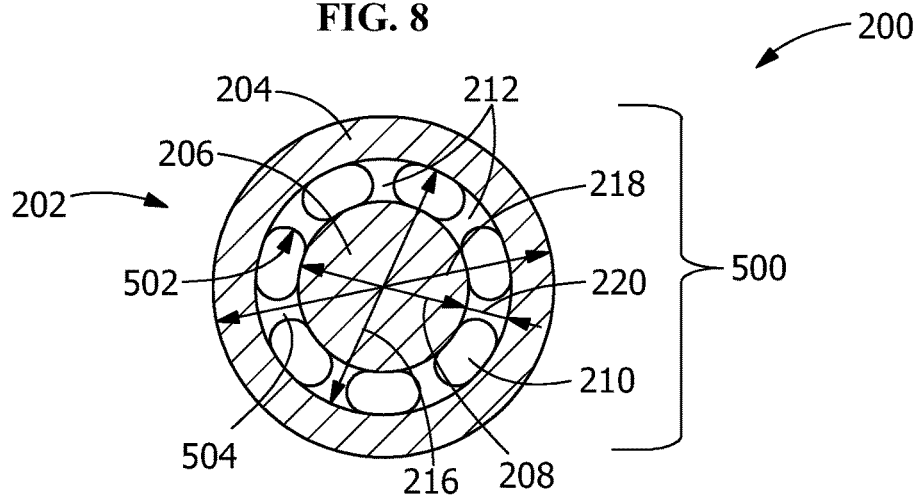
FIG. 9 is a sectional view along lines 9-9 of the preform master pattern of FIG. 2, according to an embodiment of the present disclosure.

Referring to FIG. 9, in one embodiment, a radial cluster 500 of a plurality of struts 212 in a preform master pattern 200 includes a preform wall outer diameter 218 of about 8 mm and the preform core 206 includes a preform core diameter of about 4 mm. The radial cluster 500 of the plurality of struts 212 includes seven struts 212 distributed symmetrically about the core at 51.43° intervals.

Referring to FIGS. 2 and 3, the preform wall outer diameter 218 may be any suitable diameter, including, but not limited to, for a single preform annulus 210, a diameter of between about 4 mm to about 20 mm. In one embodiment, the preform annular gap 220 between the preform core 206 and the preform wall 204 may be as large as about 5 mm, and the preform core 206 may have a preform core diameter 208 as large as about 10 mm. In another embodiment, the preform annular gap 220 may be as small as about 0.5 mm, the preform core diameter 208 may be as small as about 2 mm, and the preform wall outer diameter 218 may be as small as about 4 mm. In one embodiment, the preform wall outer diameter 218 will increase commensurate with the number of stacked preform annuli 210.

Figure 10:
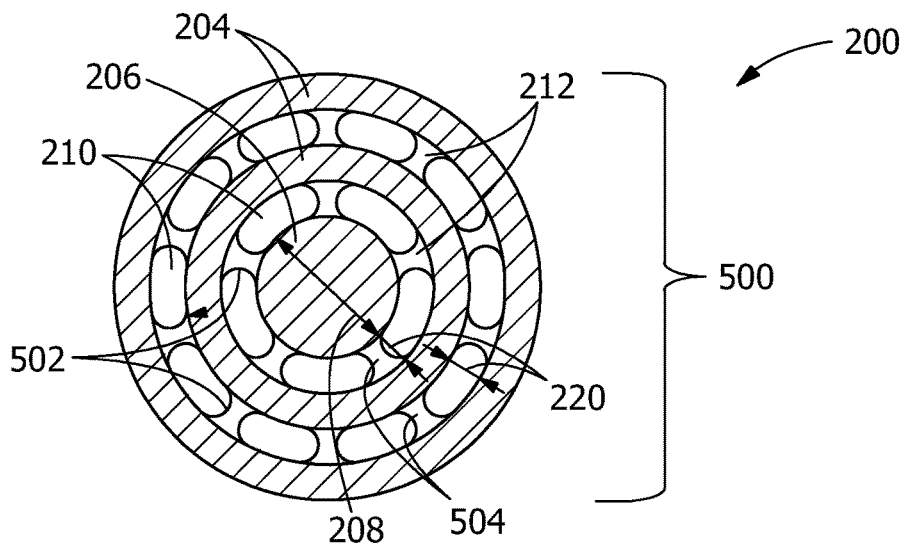
FIG. 10 is an end view of a preform master pattern including two preform walls and two annuli, according to an embodiment of the present disclosure.

Referring to FIGS. 2 and 10, the preform master pattern 200 may include any suitable number of the at least one preform wall 204. In one embodiment (FIG. 2), wherein the preform master pattern 200 includes a single preform wall 204, the preform master pattern includes a single preform annulus 210. In another embodiment (FIG. 10), wherein the preform master pattern 200 includes a plurality of the at least one preform wall 204, the preform master pattern 200 also includes a plurality of stacked preform annuli 210, with one preform annulus 210 for each of the plurality of the at least one preform wall 204. In an embodiment including a plurality of stacked preform annuli 210 and a plurality of the at least one preform wall 204, the stacked preform annuli 210 may include the same preform annular gap 220 or distinct preform annular gaps 220 interspersed amongst the plurality of the at least one preform wall 204. In one embodiment, as shown in FIG. 2, the preform master pattern 200 includes two preform walls 204 and two stacked preform annuli 210, although any suitable additional number of stacked preform walls 204 and preform annuli 210 (e.g., three, four, five, or more) may also be included.

In one embodiment, a preform master pattern 200 having two stacked preform annuli 210 may include about a 2 mm preform core 206 with about a 0.5 mm preform annular gap 220, and a preform wall outer diameter 218 of about 6 mm. In another embodiment, a preform master pattern 200 having three stacked annuli 106 may include about a 2 mm preform core 206 with about 0.5 mm preform annular gaps 220, and a preform wall outer diameter 218 of about 8 mm.

In another embodiment, a preform master pattern 200 having one preform annulus 210 may include about a 4 mm preform core 206 with about a 1 mm preform annular gap 220, and a preform wall outer diameter of about 8 mm. In still another embodiment, a preform master pattern 200 having two stacked preform annuli 210 may include about a 4 mm preform core 206 with about 1 mm annular gaps 220, and a preform wall outer diameter 218 of about 12 mm. In yet another embodiment, a preform master pattern 200 having three stacked preform annuli 210 may include about a 4 mm preform core 206 with about 1 mm annular gaps 220, and a preform wall outer diameter 218 of about 16 mm.

Referring again to FIGS. 5-10, the radial clusters 500 may include any suitable number of struts 212, including, but not limited to, one strut 212, two struts 212, three struts 212, four struts 212, five struts 212, six struts 212, seven struts 212, eight struts 212, nine struts 212, or ten or more struts 212.

Successive radial clusters 500 may be separated from one another by any suitable distance. In one embodiment, the successive radial clusters 500 are separated from one another by at least about 0.5 mm, alternatively by about 0.75 mm. The separation between successive radial clusters 500 may be constant or may vary along the preform wall length 214 of the preform master pattern 200.

The plurality of struts 212 may include any suitable geometry. In one embodiment, the plurality of struts 212 include a concave radial curvature 502. The concave radial curvature 502 of the plurality of struts 212 defines a narrowest point 504 of the plurality of struts 212. The narrowest point 504 of the plurality of struts 212 may include any suitable width. In one embodiment, the narrowest point 504 of the plurality of struts 212 includes a width of about 0.25 mm to about 0.75 mm, alternatively about 0.5 mm.

In one embodiment, wherein each subsequent radial cluster 500 includes the same number of the plurality of struts 212 and the same radial distribution of the plurality of struts 212, each subsequent radial cluster 500 is radially offset by half the radial distribution. Referring to FIG. 8, wherein the radial distribution is 72°, each subsequent radial cluster 500 would be radially offset by 36°. Referring to FIG. 9, wherein the radial distribution is 51.43°, each subsequent radial cluster 500 would be radially offset by 25.715° (shown in FIG. 10).

Figure 11:
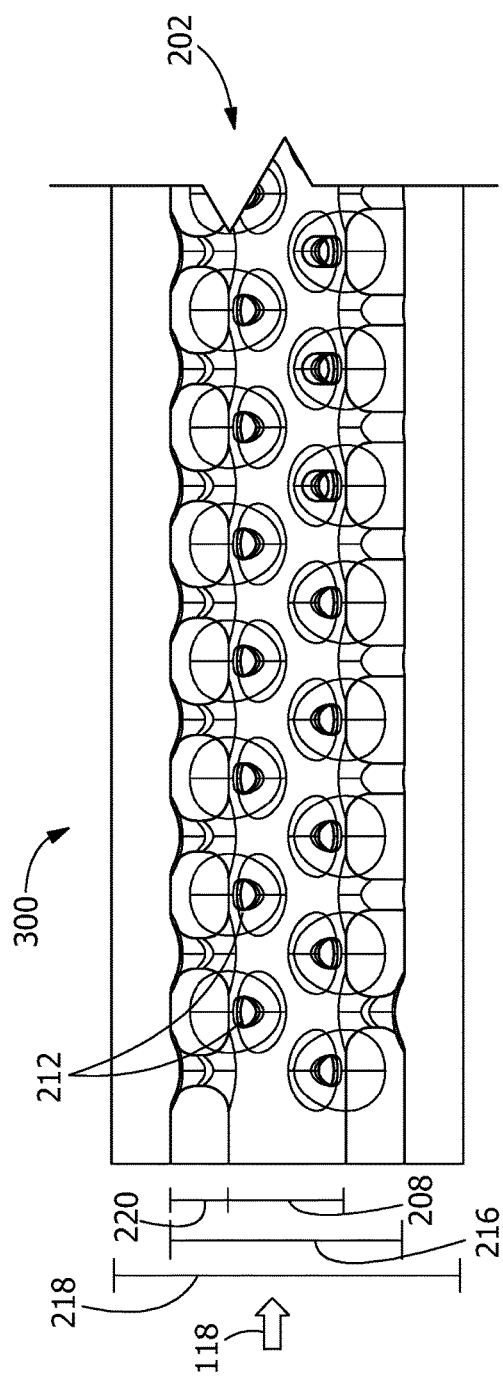
FIG. 11 is a side plan view of a preform, according to an embodiment of the present disclosure.
Figure 12:
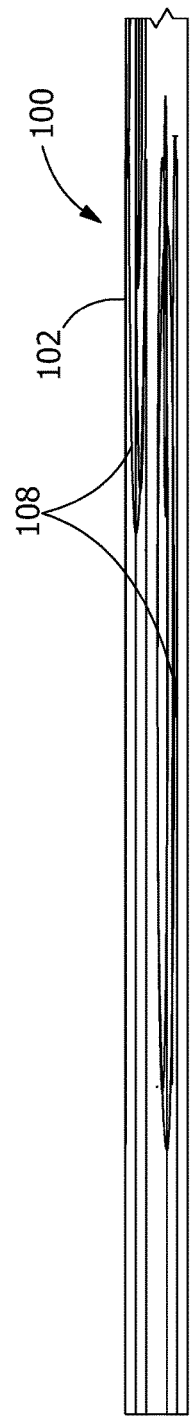
FIG. 12 is a side plan view of a reticulated annular capillary GC column formed from the preform of FIG. 11, according to an embodiment of the present disclosure.

Referring to FIGS. 11-12 (shown with transparent outer walls), in one embodiment, drawing down a preform 300 to form the reticulated annular capillary GC column 100 narrows the preform 300 by a factor of a least about 3 and lengthens the preform 300 by a factor of at least about 9, alternatively narrows the preform 300 by a factor of about 4 and lengthens the preform 300 by a factor of about 16.

The reticulated annular capillary GC column 100 may include a plurality of capillary walls 102 and a plurality of stacked annuli 106 (e.g., a reticulated annular capillary GC column 100 formed from the preform master pattern 200 of FIG. 10). The reticulated annular capillary GC column 100 may include any suitable number capillary walls 102 and annuli 106, provided that there is one annulus 106 for each capillary wall 102. In one embodiment, the reticulated annular capillary GC column 100 includes two capillary walls 102, forming two annuli 106. In another embodiment, the reticulated annular capillary GC column 100 includes three capillary walls 102 forming three annuli 106. The reticulated annular capillary GC column 100 may include more than three capillary walls 102 and more than three annuli 106. In an embodiment (not shown) in which the reticulated annular capillary GC column 100 includes a plurality of capillary walls 102, the capillary wall 102 or capillary walls 102 disposed between the core 104 and the outermost capillary wall 102 may include apertures along the wall lengths 100 of such capillary walls 102 to allow intermixing of fluids flowing through the separate annuli 106, such that the reticulated flow path 118 crosses between annuli 106. Fluidic communication between the annuli 106 may reduce or eliminate band dispersion otherwise caused by differential flow rates through the annuli 106 along the wall length 110.

In one embodiment, wherein the reticulated annular capillary GC column 100 includes two capillary walls 102, forming two stacked annuli 106, it is anticipated that in comparison to a column having the same cross-sectional open volume but not including a core 104 and not including more than one capillary wall 102, the run-time will be reduced six-fold, increasing peak height of the GC spectra six-fold, and thereby increasing signal-to-noise by a factor of six.

Casting the preform 300 from the preform master pattern 200 may include any suitable casting technique, including, but not limited to, investment casting, lost wax casting, lost foam casting, or combinations thereof. The preform 300 may be formed from any material suitable for use in a GC capillary column, including, but not limited to, glass, synthetic quartz, fused silica, stainless steel, passivated stainless steel, or combinations thereof.

In additional to reticulated annular capillary GC columns 100, the methods disclosed herein may also be extended to the formation of annular capillary columns for use with supercritical fluid chromatography and liquid chromatography. Preparation of reticulated annular capillary supercritical fluid columns would be differentiated from reticulated annular capillary GC columns 100 in that the annular gap 120 for the annuli 106 would be reduced to about 0.100 mm and below. Preparation of reticulated annular capillary liquid chromatography columns would be differentiated from reticulated annular capillary GC columns 100 in that the annular gap 120 for the annuli 106 would be reduced to about 0.010 mm and below.

In another embodiment, the reticulated annular capillary GC columns 100 and methods for forming reticulated annular capillary GC columns 100 may be adapted for pre-column guard columns for use with analytical (GC or otherwise) capillary columns. By way of example, the high surface area per unit length of the reticulated annular capillary GC columns 100 disclosed herein would enable a 10 cm length of reticulated annular capillary GC column 100 to replace a 50 cm length of standard 0.25 mm inner diameter used for such a purpose. In a further embodiment, reticulated annular capillary GC column 100 adapted for use as a guard pre-column guard column may incorporated into a replaceable cartridge.

EXAMPLES

Computational fluid dynamic simulations have been performed based on the reticulated annular capillary GC column 100 of FIG. 12, except with three vanes 108 in each radial cluster 500. Based upon a reticulated annular capillary GC column 100 having a wall length 110 of 48 mm and a 0.25 mm annular gap, calculations predict that at a helium flow of 40 cm$^3$/s at 100° C., the pressure drop will be about 8.61 psi for a 30 meter long reticulated annular capillary GC column 100 with the same cross-sectional capillary dimensions. Further computational analysis calculates a total surface area of about 238 mm$^2$ and an internal volume of about 25 mm$^3$ for the reticulated annular capillary GC column 100 of FIG. 12.

The relative capacities of GC columns based on the number of struts 212 per radial cluster 500 are presented in Table 1. These calculations are based on the disclosed dimensions, and presume that each radial cluster 500 includes the same number of struts 212. The results are presented normalized relative to a 0.25 mm diameter capillary and a 0.125 mm diameter capillary without annulus 106 or struts 212. With respect to the calculations, it is notable that the column efficiency doubles when the annular gap 120 is halved.

TABLE 1

| GC Column | Relative Capacity |
|---|---|
| 0.25 mm Capillary | 1 |
| 0.25 mm, Annular Capillary, 3 struts, 1.5 mm Outer Diameter | 10.3 |
| 0.25 mm, Annular Capillary, 5 struts, 2.0 mm Outer Diameter | 17.1 |
| 0.125 mm Capillary | 0.25 |
| 0.125 mm, Annular Capillary, 3 struts, 0.75 mm Outer Diameter | 2.6 |
| 0.125 mm, Annular Capillary, 5 struts, 1.0 mm Outer Diameter | 4.3 |
| 0.063 mm, Annular Capillary, 5 struts, 0.5 mm Outer Diameter | 1.07 |

The back pressures (psi) of GC columns, presuming operation at 100° C. over different column lengths and diameters, have been calculated, comparing non-annular capillary GC columns ("Capillary") with reticulated annular capillary GC columns 100 ("Annular") the results of which calculations are presented in Table 2.

TABLE 2

| Column | Helium (40 cm$^3$/s) | Helium (30 cm$^3$/s) | Hydrogen (40 cm$^3$/s) |
|---|---|---|---|
| 0.25 mm Capillary, 30 m | 21.96 | 16.17 | 9.49 |
| 0.25 mm Annular, 30 m | 8.61 | 6.34 | 3.72 |
| 0.13 mm Capillary, 30 m | 99.63 | 66.87 | 38.22 |
| 0.13 mm Annular, 30 m | 39.05 | 26.20 | 14.98 |
| 0.13 mm Annular, 15 m | 19.53 | 13.10 | 7.49 |
| 0.063 mm Annular, 15 m | 78.12 | 52.40 | 29.96 |
| 0.063 mm Annular, 7.5 m | 39.06 | 26.20 | 14.98 |

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A reticulated annular capillary gas chromatography ("GC") column, comprising:
   at least one capillary wall including a wall length, a wall inner diameter, and a wall outer diameter;
   a core disposed within the capillary wall, the core including a core outer diameter;
   at least one annulus disposed between the at least one capillary wall and the core; and
   a plurality of vanes disposed in the at least one annulus, each of the plurality of vanes extending along the wall length and for less than the wall length, the plurality of vanes defining a reticulated flow path through the at least one annulus,
   wherein the plurality of vanes structurally support the core within the at least one capillary wall.

2. The reticulated annular capillary GC column of claim 1, further including a plurality of capillary walls and a plurality of annuli.

3. The reticulated annular capillary GC column of claim 2, wherein the reticulated flow path crosses between annuli along the wall length.

4. The reticulated annular capillary GC column of claim 1, wherein the reticulated annular capillary GC column includes a material selected from the group consisting of glass, synthetic quartz, fused silica, stainless steel, passivated stainless steel, and combinations thereof.

5. The reticulated annular capillary GC column of claim 1, further including an annular gap of greater than 0.100 mm.

6. A method for forming a reticulated annular capillary gas chromatography column, comprising:
   forming a preform master pattern by an additive manufacturing technique, the preform master pattern including an antecedent conformation, the antecedent conformation including:
      at least one preform wall;
      a preform core having a preform core diameter disposed within the at least one preform wall;
      at least one preform annulus disposed between the at least one preform wall and the preform core; and
      a plurality of struts disposed in the at least one preform annulus,
      wherein the plurality of struts structurally support the preform core within the at least one preform wall;
   casting a preform from the preform master pattern, the preform including the antecedent conformation;
   drawing down the preform, forming the reticulated annular capillary gas chromatography column, drawing down the preform including:
      lengthening and narrowing the at least one preform wall, forming at least one capillary wall, the at least one capillary wall including a wall length, a wall inner diameter, and a wall outer diameter;
      lengthening and narrowing the preform core to form a core, narrowing the preform core diameter to a core outer diameter;
      lengthening and narrowing the plurality of struts, forming a plurality of vanes, each of the plurality of vanes extending along the wall length and for less than the wall length, the plurality of vanes defining a reticulated flow path through the at least one annulus,
      wherein the plurality of vanes structurally support the core within the at least one capillary wall.

7. The method of claim 6, wherein the additive manufacturing technique includes a technique selected from the group consisting of three-dimensional printing, fused deposition modeling, fused filament fabrication, stereolithography, continuous liquid interface production, and combinations thereof.

8. The method of claim 6, wherein forming the preform master pattern include forming the preform master pattern interpolated with a support material, and removing the support material.

9. The method of claim 8, wherein the support material includes a wax material.

10. The method of claim 8, wherein removing the support material includes submerging the preform master pattern interpolated with the support material in a solvent bath, dissolving the support material, and isolating the preform master pattern.

11. The method of claim 6, wherein the plurality of struts are organized into radial clusters along the preform wall length in which each radial cluster is distributed about the preform core.

12. The method of claim 11, wherein the radial clusters are alighted with one another.

13. The method of claim 11, wherein the radial clusters are offset from one another.

14. The method of claim 13, wherein the offset between each subsequent radial cluster is constant.

15. The method of claim 11, wherein successive radial clusters are separated from one another by at least about 0.5 mm.

16. The method of claim 6, wherein the plurality of struts includes a concave radial curvature defining a narrowest point of the plurality of struts, the narrowest point of the plurality of struts including a width of about 0.25 mm to about 0.75 mm.

17. The method of claim 6, wherein drawing down the preform narrows the preform by a factor of at least about 3 and lengthens the preform by a factor of at least about 9.

18. The method of claim 6, wherein casting the preform from the preform master pattern includes a casting technique selected from the group consisting of investment casting, lost wax casting, lost foam casting, and combinations thereof.

19. The method of claim 6, wherein casting the preform includes forming the preform from a material selected from the group consisting of glass, synthetic quartz, fused silica, stainless steel, passivated stainless steel, and combinations thereof.

20. The method of claim 6, further including forming a preform master pattern having a plurality of preform walls and a plurality of preform annuli, and forming a plurality of capillary walls and a plurality of annuli in the reticulated annular capillary GC column.

* * * * *